US010549075B2

(12) United States Patent
Murphy

(10) Patent No.: US 10,549,075 B2
(45) Date of Patent: Feb. 4, 2020

(54) MEDICAL GUIDEWIRE DISPENSER

(71) Applicant: M MICRO TECHNOLOGIES, INC., Pompano Beach, FL (US)

(72) Inventor: Jason Murphy, Grand Rapids, MI (US)

(73) Assignee: M MICRO TECHNOLOGIES, INC., Pompano Beach, FL (US)

( * ) Notice: Subject to any disclaimer, the term of this patent is extended or adjusted under 35 U.S.C. 154(b) by 831 days.

(21) Appl. No.: 14/849,165

(22) Filed: Sep. 9, 2015

(65) Prior Publication Data

US 2017/0065794 A1  Mar. 9, 2017

(51) Int. Cl.
*A61M 25/09* (2006.01)
*A61M 25/00* (2006.01)

(52) U.S. Cl.
CPC .... *A61M 25/09041* (2013.01); *A61M 25/002* (2013.01)

(58) Field of Classification Search
CPC ........ A61M 25/09; A61M 2025/09175; A61M 2025/09083; A61M 25/09041
USPC ......................................................... 600/585
See application file for complete search history.

(56) References Cited

U.S. PATENT DOCUMENTS

| 1,340,297 | A | 5/1920 | Schiff |
| 2,802,638 | A | 8/1957 | Ireland |
| 3,321,185 | A | 5/1967 | Zenke |
| 3,576,295 | A | 4/1971 | Hale |
| 4,903,826 | A | 2/1990 | Pearce |
| 5,730,150 | A | 3/1998 | Peppel et al. |
| 6,405,414 | B1 * | 6/2002 | Byrnes ................. A61M 25/00 24/339 |
| 2005/0081990 | A1 | 4/2005 | Ruotsalainen |
| 2007/0193903 | A1 | 8/2007 | Opie et al. |
| 2009/0105654 | A1 * | 4/2009 | Kurth .................... A61M 25/09 604/170.03 |
| 2010/0305474 | A1 | 12/2010 | DeMars et al. |

* cited by examiner

*Primary Examiner* — Daniel L Cerioni
(74) *Attorney, Agent, or Firm* — BakerHostetler

(57) ABSTRACT

A dispensing apparatus including a body having an open end and a closed end; a first channel and a second channel within the body, the first and second channels sharing a sidewall and the first channel defining the open end; and a wire disposed within the first and second channels. This disclosure also discloses a dispensing apparatus including a body having an open end and a closed end and a first layer and a second layer; a first channel and a second channel within the first layer and a third channel and a fourth channel within the second layer, the first channel defining the open end; a transitional segment providing fluid communication between the first and second layers; and a wire disposed within the first, second, third, and fourth channels.

7 Claims, 4 Drawing Sheets

MEDICAL GUIDEWIRE DISPENSER

FIELD OF THE DISCLOSURE

This disclosure relates to dispensing apparatuses. In particular, this disclosure is directed to medical guidewire dispensers.

BACKGROUND

A commonly used technique for inserting a catheter into a blood vessel, referred to as the Seldinger technique, involves inserting a hollow needle to puncture the blood vessel, inserting a thin guidewire into the vessel through the hollow needle, removing the needle, guiding the catheter over the guidewire into the blood vessel and, finally, removing the guidewire. Guidewires may also be used in cardiovascular surgery procedures. For example, a surgeon may make an incision in a patient's leg. The surgeon may then insert a guidewire into the incision and feed the guidewire through an artery or vein until the guidewire reaches the desired location. In one example of a cardiovascular operation where guidewires may be used, a stent may be attached to the guidewire. Once the guidewire reaches the desired location, the stent may be expanded, for example, by injecting air into the stent. Another example of medical guidewire applications is in the field of biopsies. One end of the guidewire may have a jaw or a clamp. The jaw or clamp may be used to remove a sample of a tissue from a patient.

Existing dispensers suffer from problems arising during shipment or storage. These devices typically are assembled from multiple components, including a coiled tube. Plastic clips are usually provided to keep the tubes from uncoiling. Due to the compressive force on the coiled tube, the components of these dispensers tend to separate during shipment and storage. Particularly, the tube will dislodge from the clips. This often results in a bending of the enclosed guidewire, rendering the wire unusable. If the dispenser comes apart during use, the guidewire may fall to the floor or otherwise be exposed to non-sterile conditions.

Traditional guidewire dispensers also have problems related to their dimensions and weight. For example, the clips used to hold the tubes of traditional guidewire dispensers in a coiled formation may be approximately ¼ inch thick. Thus, the clips used to keep the tubes coiled add a significant amount of thickness to the overall package of traditional guidewire dispensers. Thus, traditional guidewire dispensers require more boxes, more warehouse real estate, and more trucking than when compared to the guidewire dispenser of this disclosure. Additionally, the traditional guidewire dispensers are heavier than the guidewire dispenser of this disclosure. This is because traditional guidewire dispensers are manufactured using extruded tubing. Extruded tubing limits the thinness of the overall package of the guidewire dispenser.

As previously indicated, bent guidewires cannot be used. Guidewires are occasionally bent during the manufacturing process or during assembly of the dispenser. It is preferable to screen these defective guidewires prior to distribution, however, none of the traditional guidewire dispensers have any mechanism for preventing assembly of defective guidewires.

Moreover, current guidewire dispensers are quite limited in the length of guidewire that may be stored within it. For example, current guidewire dispensers are limited to housing a traditional length of guidewires, such as 1000 mm. Longer guidewires would require more coils, which would make traditional dispensers even larger and more unwieldy than they currently are. Alternatively, or additionally, the coils in traditional dispensers may have a tighter radius. A tighter radius, however, increases friction between the guidewire and the dispenser, which may cause problems during an operation.

Thus, there is a need for a guidewire dispenser that does not rely on clips to prevent the dispenser from uncoiling. Additionally, there is a need for a guidewire dispenser that can store much longer than traditional length guidewires without becoming unwieldy.

SUMMARY OF THE DISCLOSURE

In one aspect of this disclosure, a dispensing apparatus comprising: a body having an open end and a closed end; a first channel and a second channel within the body, the first and second channels sharing a sidewall and the first channel defining the open end; and a wire disposed within the first and second channels is disclosed.

In another aspect of this disclosure, a dispensing apparatus comprising: a body having an open end and a closed end and a first layer and a second layer; a first channel and a second channel within the first layer and a third channel and a fourth channel within the second layer, the first channel defining the open end; a transitional segment providing fluid communication between the first and second layers; and a wire disposed within the first, second, third, and fourth channels is disclosed

BRIEF DESCRIPTION OF THE FIGURES

This disclosure will be further described in connection with the accompanying drawings, in which.

DETAILED DESCRIPTION

The following disclosure describes a dispensing apparatus in the context of a medical guidewire dispenser. However, as one of ordinary skill in the art would readily recognize, the apparatus of this disclosure may be used to dispense items other than medical guidewires.

Figure 1:
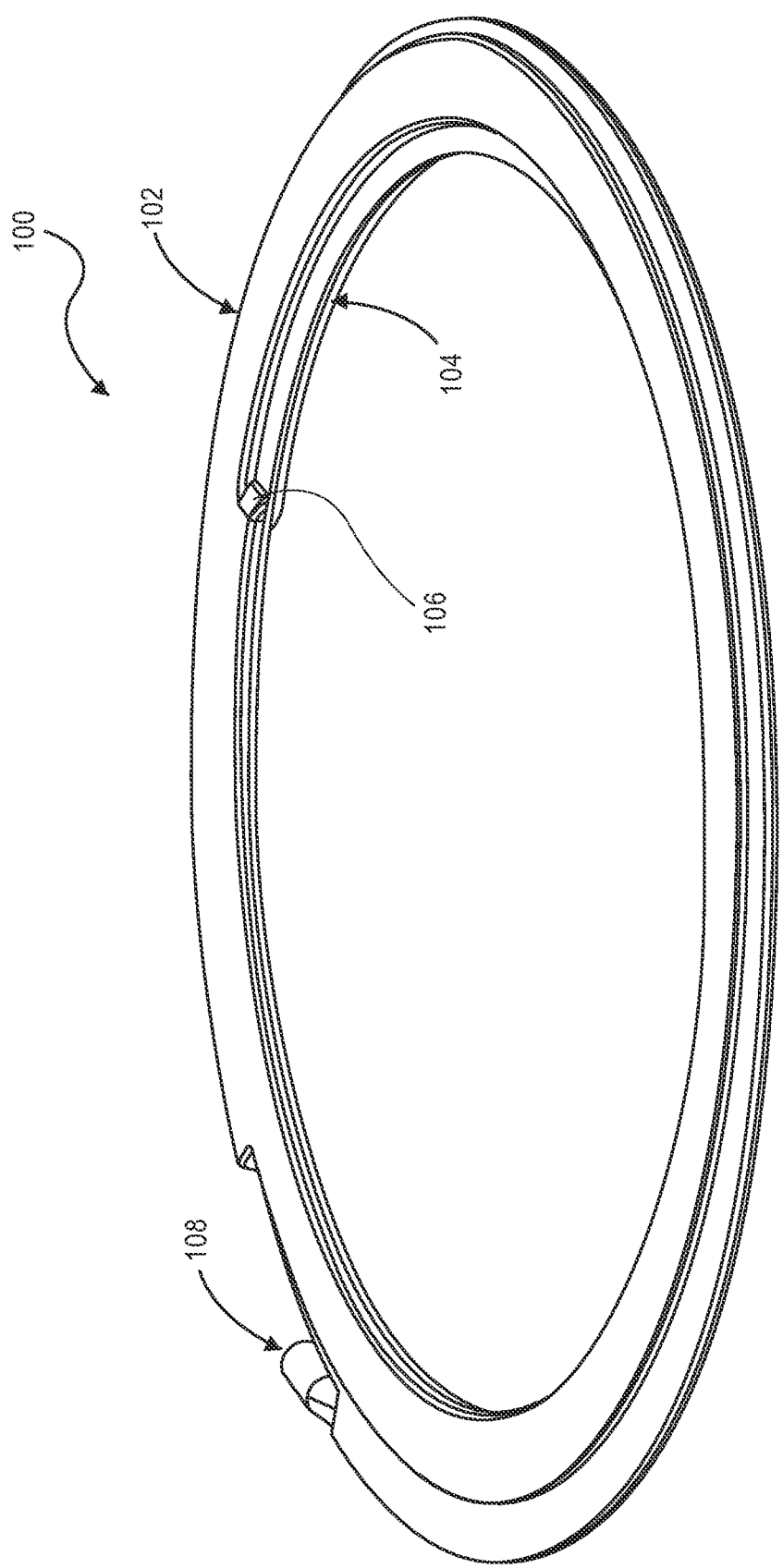
FIG. 1 illustrates a guidewire dispenser, according to one aspect of this disclosure.

FIG. 1 illustrates a guidewire dispenser 100, according to one aspect of this disclosure. The guidewire dispenser 100 may comprise a first layer 102, a second layer 104, a transitional segment 106, and an outlet port 108. The first layer 102 may be a single channel containing a guidewire. Alternatively, the first layer 102 may be multiple channels. Each of the multiple channels may contain a segment of a single guidewire. The second layer 104 may be similar to first layer 102. The second layer 104 may be a single channel containing a guidewire. Alternatively, the second layer 104 may be multiple channels. Each of the multiple channels may contain a segment of a single guidewire. In one aspect of this disclosure, the guidewire dispenser 100 may only have one layer. For example, the guidewire dispenser 100 may only have the first layer 102. Alternatively, the guidewire dispenser 100 may only have the second layer 104. One of ordinary skill in the art would recognize that the guidewire dispenser 100 may have more than two layers, as illustrated in FIG. 1. For example, the guidewire dispenser 100 may have three or more layers. In the example where the guidewire dispenser 100 has three or more layers, the guidewire dispenser 100 may have a transitional segment 106 between each of the layers.

The guidewire dispenser 100 may be manufactured using, for example, injection molding. Any suitable material may be used, such as high density polyethylene (HDPE) or low density polyethylene (LDPE). Typical guidewire dispensers have wall thicknesses ranging approximately from 40 to 50 thousandths of an inch. The wall thicknesses were limited because typical guidewire dispensers are manufactured using extruded tubing. In contrast, according to one aspect of this disclosure, the wall thicknesses of this guidewire dispenser 100 may be much thinner, for example 40%-60% thinner. Thinner thicknesses are achievable because the manufacturing process, according to one aspect of this disclosure, utilizes injection molding rather than extruded tubing. Additional benefits of using injection molding will be described herein. Since the wall thicknesses of the guidewire dispenser 100 may be much thinner than typical guidewire dispensers, the amount of material used to manufacture the guidewire dispenser 100 may be much lower. This is a significant advantage of the guidewire dispenser 100 of this disclosure. As medical device original equipment manufacturers (OEMs) become more cost-sensitive, due to regulations, OEMs may wish to reduce the cost of manufacturing guidewire dispensers. Because this guidewire dispenser 100 may be manufactured using injection molding, rather than extruded tubing, this guidewire dispenser 100 may use 40-50% less material than typical guidewire dispensers. Thus, this guidewire dispenser 100 may result in lower raw material consumption and lower processing costs. Additionally, this guidewire dispenser 100 may be fully recyclable and thus more environmentally friendly.

The outlet port 108 may be used as an exit or an entrance for guidewire. In this aspect of this disclosure, the outlet port 108 may have a circular cross section. As described below, the outlet port 108 may have a different cross section. The outlet port 108 may be used to connect the guidewire dispenser to other medical instruments.

Figure 2:
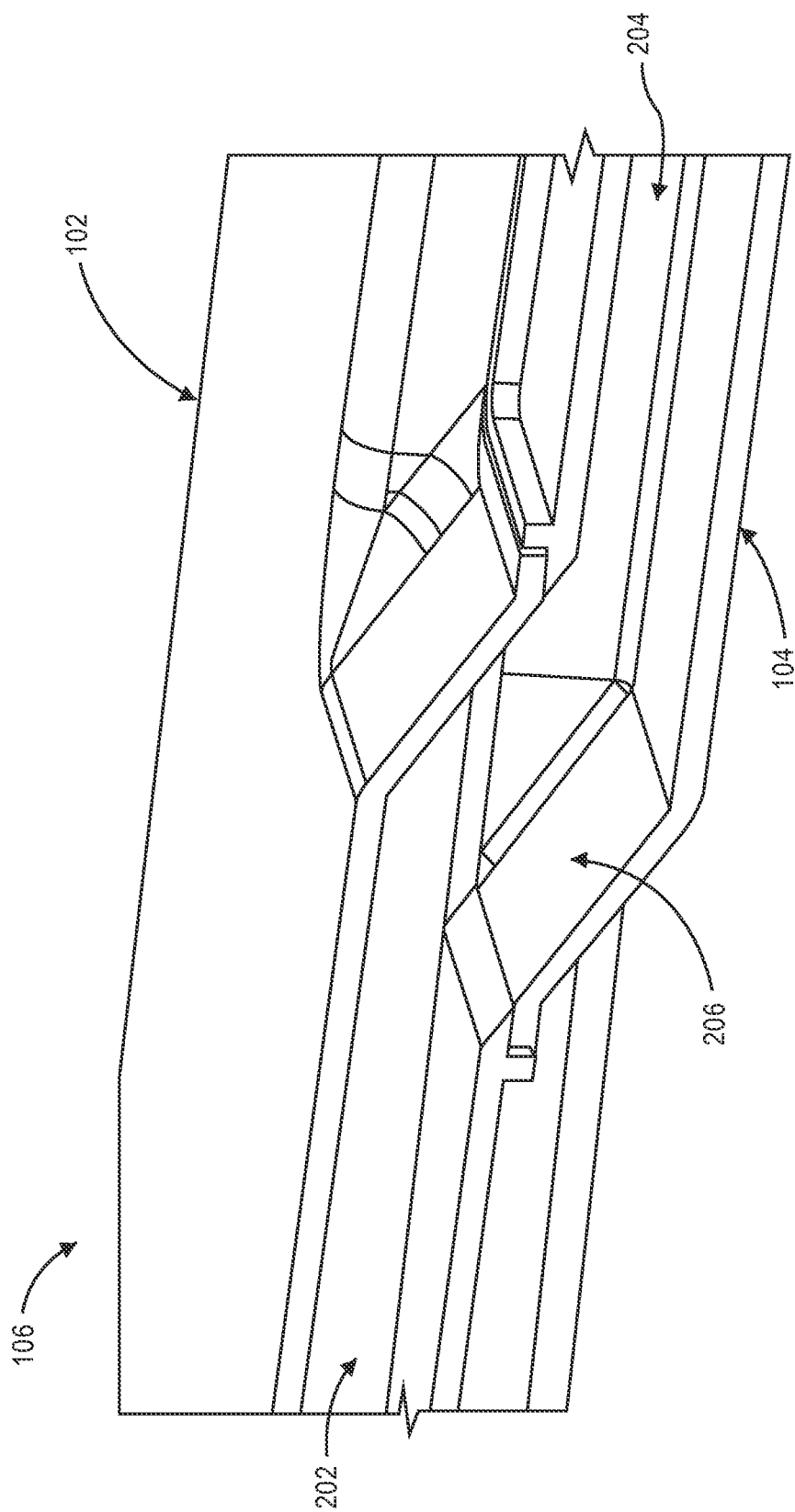
FIG. 2 illustrates a transitional segment of the guidewire dispenser, according to one aspect of this disclosure.

FIG. 2 illustrates a transitional segment 106 of the guidewire dispenser 100, according to one aspect of this disclosure. FIG. 2 shows a cross section of the guidewire dispenser 100. In this aspect, the guidewire dispenser 100 has two layers, a first layer 102 and a second layer 104. FIG. 2 shows the first layer 102, second layer 104, a channel 202 within the first layer 102, a channel 204 within the second layer 104, and a ramp 206.

The channel 202 within the first layer 102 may be in a plane different from the channel 204 within the second layer 104. Thus, the guidewire dispenser 100 may use a transitional segment 106, for example, a ramp 206, to provide fluid communication between the channel 202 within the first layer 102 and the channel 204 within the second layer 104. One of ordinary skill in the art would recognize that any suitable transitional segment, not just the ramp 206 shown in FIG. 2, may be implemented in the guidewire dispenser 100 to provide fluid communication between the channel 202 within the first layer 102 and the channel 204 within the second layer 104. The guidewire may traverse the transitional segment 106 to go from the first layer 102 to the second layer 104.

Guidewires are becoming longer. Historically, guidewires generally were approximately 1-1.5 meters in length. However, as medical operations become more complex, longer guidewires are required. Thus, guidewires have grown to be approximately 3 meters in length. Guidewire dispensers need to remain small so that they do not become cumbersome and unwieldy to use. Thus, to accommodate longer length guidewires, traditional guidewire dispensers would have to either become larger or more tightly coil the guidewire. Both are undesirable. If traditional guidewire dispensers became larger, then the packaging of the guidewire dispensers would have to be customized. If traditional guidewire dispensers more tightly coiled the guidewire, the guidewire would be subject to more stress. The inner diameter of the guidewire would become much smaller, which puts more stress on the guidewire. Additionally, a smaller inner diameter results in increased tension, drag, and/or friction between the guidewire and the guidewire dispenser.

Because of the transitional segment 106, this guidewire dispenser 100 may double the length of guidewire housed without increasing the size of the packaging or by more tightly coiling the guidewire. Alternatively, in other aspects of this disclosure, this guidewire dispenser 100 may have more than two layers 102 and 104. For example, if there are three layers, this guidewire dispenser 100 may triple the guidewire length stored as compared to traditional guidewire dispensers.

Figure 3:
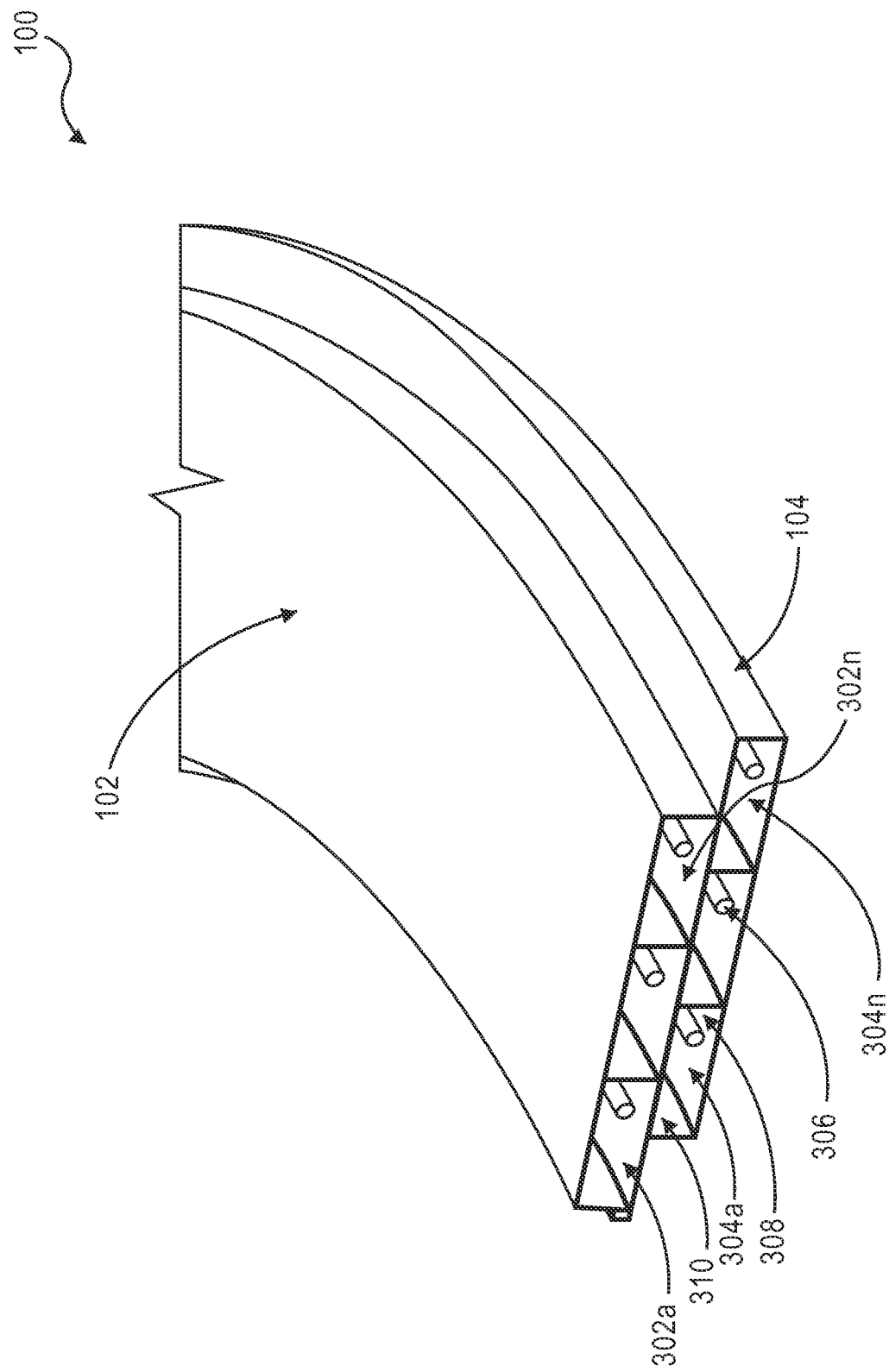
FIG. 3 is a cross-sectional view of the guidewire dispenser, according to one aspect of this disclosure.

FIG. 3 is a cross-sectional view of the guidewire dispenser 100, according to one aspect of this disclosure. FIG. 3 shows a guidewire dispenser 100 with a first layer 102 and a second layer 104. Each of the layers 102 and 104 may have one or more channels $302a \ldots n$ and $304a \ldots n$, respectively, where n is the total number of channels for a layer. For example, in this aspect, first layer 102 has three channels 302 and second layer 104 has three channels 304. The number of channels $302n$ may not be the same as the number of channels $304n$. Each channel 302 and 304 may be defined by one or more vertical walls 308 and one or more horizontal walls 310. For example, in this aspect, channel 302a is defined by four walls: two vertical walls 308 and two horizontal walls 310. In this aspect, channel 302a has a rectangular cross section. A width of the channel $302a \ldots n$ and $304a \ldots n$ may be approximately 60 thousandths of an inch to 80 thousandths of an inch. Other cross sectional shapes, such as square, circular, or any other closed polygonal shape, may be used. Within each of the channels $302a \ldots n$ and $304a \ldots n$ may be a portion of a guidewire 306.

As shown in FIGS. 1-3, the guidewire dispenser 100 does not use clips to hold the channels $302a \ldots n$ and $304a \ldots n$ together. The guidewire dispenser does not need clips because the guidewire dispenser is manufactured using injection molding rather than extruded tubing. The guidewire dispenser 100 may be manufactured as a single piece. Alternatively, the guidewire dispenser 100 may be manufactured using several pieces. The several pieces may then be, for example, welded together using a laser weld, ultrasonic welding, ultraviolet cured glue, or heat staking Since there are no clips, as in traditional guidewire dispensers, the tubes will not become dislodged during shipment or handling. Thus, the guidewire 306 will not be bent and rendered unusable. Additionally, the guidewire dispenser 100 will not come apart during use. Thus, the guidewire 306 will not fall to the floor or be exposed to non-sterile conditions.

Figure 4:
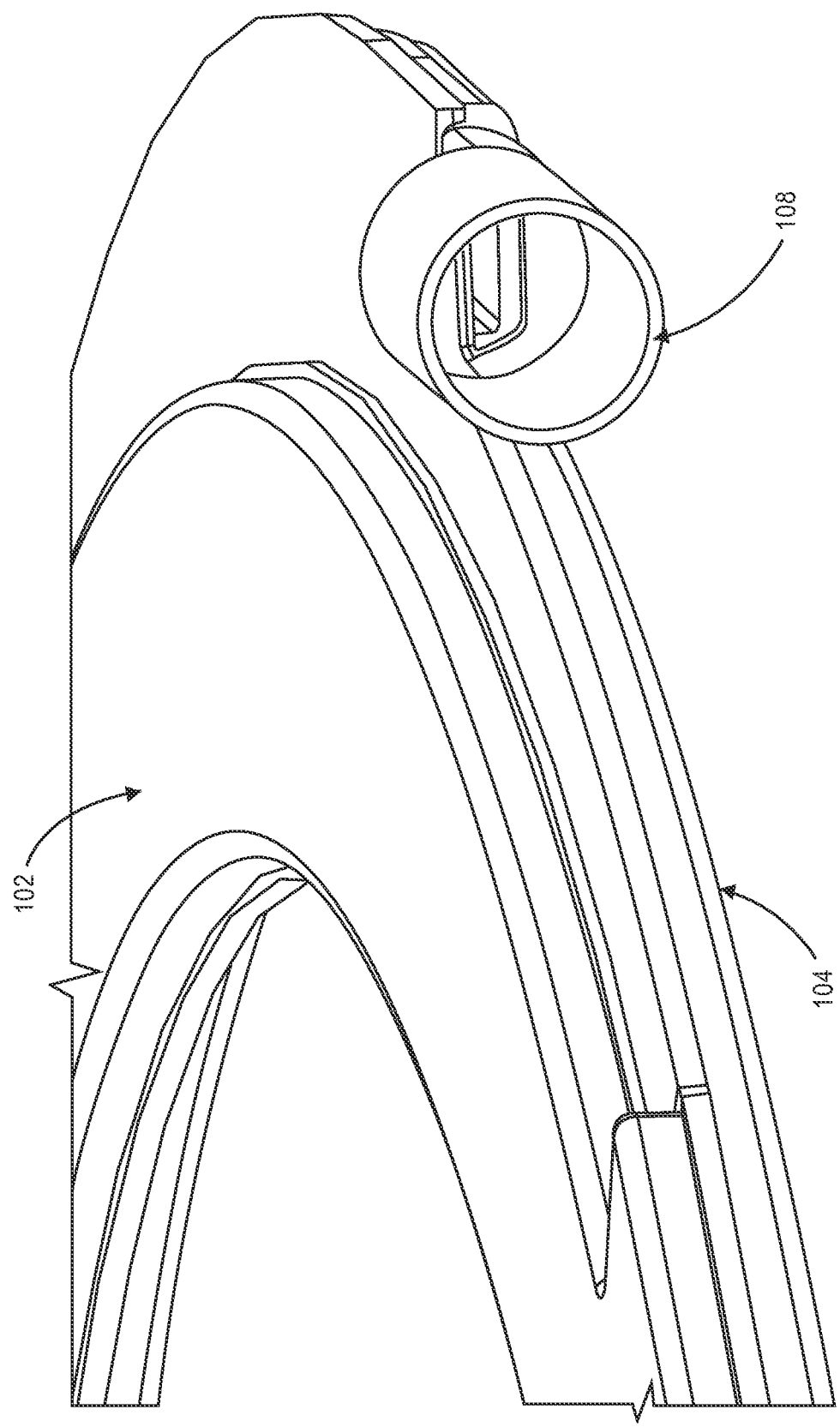
FIG. 4 illustrates an outlet port of the guidewire dispenser, according to one aspect of this disclosure.

FIG. 4 illustrates an outlet port 108 of the guidewire dispenser 100, according to one aspect of this disclosure. The outlet port 108 may be the point of filling the guidewire dispenser 100 with a guidewire 306. Alternatively, it may be the point of removing the guidewire 306 from the guidewire dispenser 100. In traditional guidewire dispensers, the outlet port 108 may have a circular cross section, as illustrated in FIG. 4. Various medical instruments, for example, a syringe, a valved port sometimes known as a stopcock, a payoff wheel, or any other device with a standard Leur taper and thread, may attach to the guidewire dispenser 100 at the outlet port 108. In traditional guidewire dispensers, the cross sectional shape of the outlet port may not be changed during design. The outlet port generally had a circular cross section because the guidewire dispenser was manufactured using extruded tubing. In contrast, the outlet port 108 of the guidewire dispenser 100 of this disclosure may have various cross sectional shapes. For example, the outlet port 108 may have an oval cross section, a rectangular cross section, or any other cross sectional shape which may be useful to attach the guidewire dispenser 100 to a medical instrument. Other modifications to the outlet port 108 may be possible. For example, the outlet port 108 may be threaded, it may be tapered, also known as a Luer, or it may have an internal and external thread.

Various modifications and alterations to the present disclosure may be appreciated based on a review of this disclosure. These changes and additions are intended to be within the scope and spirit of this disclosure as defined by the following claims.

I claim:

1. A dispensing apparatus comprising:
   a single-piece body having an open end and a closed end;
   a first channel and a second channel within the body, the first and second channels sharing a sidewall and the first channel defining the open end, wherein the first channel and the second channel are fully enclosed and do not include clips;
   wherein a cross sectional shape of the first and second channels is rectangular;
   an outlet port disposed directly at the open end and having a cross sectional shape transitioning directly from the rectangular cross sectional shape of the first channel to a circular cross sectional shape of the outlet port; and
   a wire disposed within the first and second channels.

2. The apparatus of claim 1, wherein the first and second channels are coiled.

3. The apparatus of claim 1, wherein the body is injection molded.

4. The apparatus of claim 1, wherein the open end is threaded or of Luer type.

5. The apparatus of claim 1, wherein the wire is a guidewire.

6. The apparatus of claim 1, wherein the first and second channels are laser welded together.

7. The apparatus of claim 1, wherein a width of the first or second channel is between 60 thousandths of an inch to 80 thousandths of an inch.

* * * * *